(12) United States Patent
McConnell et al.

(10) Patent No.: US 10,591,497 B2
(45) Date of Patent: Mar. 17, 2020

(54) IMMUNOASSAY FOR SYNTHETIC CANNABINOIDS OF THE ADAMANTYL INDAZOLE/INDOLE-3-CARBOXAMIDE FAMILY

(71) Applicant: Randox Laboratories Limited, Crumlin (GB)

(72) Inventors: Ivan McConnell, Crumlin (GB); Elouard Benchikh, Crumlin (GB); Philip Lowry, Crumlin (GB); Peter Fitzgerald, Crumlin (GB)

(73) Assignee: RANDOX LABORATORIES LTD., Northern Ireland (GB)

( * ) Notice: Subject to any disclaimer, the term of this patent is extended or adjusted under 35 U.S.C. 154(b) by 330 days.

(21) Appl. No.: 14/723,609

(22) Filed: May 28, 2015

(65) Prior Publication Data
US 2015/0346227 A1  Dec. 3, 2015

(30) Foreign Application Priority Data

May 28, 2014 (GB) .................................. 1409464.3
May 29, 2014 (GB) .................................. 1409514.5

(51) Int. Cl.
| | | |
|---|---|---|
| G01N 33/94 | (2006.01) | |
| A61K 39/385 | (2006.01) | |
| C07D 231/56 | (2006.01) | |
| C07K 16/44 | (2006.01) | |

(52) U.S. Cl.
CPC ......... *G01N 33/948* (2013.01); *A61K 39/385* (2013.01); *C07D 231/56* (2013.01); *C07K 16/44* (2013.01); *C07K 2317/30* (2013.01); *C07K 2317/33* (2013.01); *C07K 2317/92* (2013.01)

(58) Field of Classification Search
CPC ............ A61K 39/385; A61K 47/48284; C07D 231/56; C07K 16/44; C07K 2317/30; C07K 2317/33; C07K 2317/92; G01N 33/948
See application file for complete search history.

(56) References Cited

U.S. PATENT DOCUMENTS

| | | | | |
|---|---|---|---|---|
| 9,079,964 | B2 * | 7/2015 | Benchikh ............ | G01N 33/948 |
| 9,434,687 | B2 * | 9/2016 | Benchikh ............ | C07D 209/12 |
| 9,441,033 | B2 * | 9/2016 | Benchikh ............ | C07D 209/12 |
| 2004/0236101 | A1 * | 11/2004 | Makriyannis ........ | C07D 231/56 544/60 |
| 2012/0040378 | A1 * | 2/2012 | Benchikh ............ | C07K 16/44 435/7.92 |
| 2016/0084859 | A1 * | 3/2016 | McConnell ............ | C07K 16/44 435/7.93 |

FOREIGN PATENT DOCUMENTS

| | | |
|---|---|---|
| EP | 2487155 A1 | 8/2012 |
| EP | 2698384 A1 | 2/2014 |

OTHER PUBLICATIONS

Goodrow et al., "Strategies for Immunoassay Hapten Design," in Immunoanalysis of Agrochemicals; Nelson, J., et al.; ACS Symposium Series, 1995, vol. 586, Chapter 9, pp. 119-139.*
Szurdoki et al., "Important Factors in Hapten Design and Enzyme-Linked Immunosorbent Assay Development," in Immunoanalysis of Agrochemicals; Nelson, J., et al.; ACS Symposium Series, 1995, vol. 586, Chapter 4, pp. 39-63.*
Englebienne, "Immune and Receptor Assays in Theory and Practice," CRC Press, 2000, p. 308.*
Tulip, Data Sheet Anti-AKB48 Synthetic Cannabinoid, IgG, Rabbit polyclonal Antibody, Cat. #1087) dated 140314J and posted on Internet (http://www.tulipbiolabs.com/ webassets/1087.pdf) on Mar. 14, 2014.*
C. V. Rao, "Immunology, A textbook", Alpha Science Internatl. Ltd., 2005, pp. 63, 69-71.*
A print-out retrieved from https://en.wikipedia.org/wiki/IC50 on Mar. 12, 2018.*
A kit description "AKB48 (APINAKA) Synthetic Cannabinoid ELISA Kit," dated Feb. 25, 2015.*
Goldsby et al., "Immunology," W.H. Freeman & Co., 2003, 5th Edition, p. 69.*
Amato, et al., "NMR Assignment of N-(1-adamantyl)-1-pentyl-1H-indazole-3-carboxamide Seized as Herbal Incense for the First Time in Italy", Journal of Forensic Science & Criminology, vol. 1, Issue 4, Feb. 13, 2014, 1-6.
Bellia, "GB Search Report for GB1409464.3", dated Feb. 5, 2015.
Gandhi, et al., "First Characterization of AKB-48 Metabolism, a Novel Synthetic Cannabinoid, Using Human Hepatocytes and High-Resolution Mass Spectrometry", The AAPS Journal, 2013, vol. 15(4), DOI: 10.1208/s12248-013-9516-0, Jul. 15, 2013, 1091-1098.
Gandhi, et al., "High-resolution mass spectrometric metabolite profiling of a novel synthetic designer drug, N-(adamantan-1-yl)-1-(5-fluoropentyl)-1 Hindole-3-carboxamide (STS-135), using cryopreserved human hepatocytes and assessment of metabolic stability with human . . . ", Drug Testing and Analysis (2014), Published online in Wiley Online Library, DOI 10.1002/dta.1662, Apr. 3, 2014, 1-12.
Grigoryev, et al., "The detection of the urinary metabolites of 3-[(adamantan-1-yl)carbonyl]-1-pentylindole (AB-001 ), a novel cannabimimetic, by gas chromatography-mass spectrometry", Drug Testing and Analysis, 2012, vol. 4, Published online in Wiley Online Library, DOI 10.1002/dta.350, Nov. 18, 2011, 519-524.
Holm, et al., "Metabolites of SF-AKB-48, a synthetic cannabinoid receptor agonist, identified in human urine and liver microsomal preparations using liquid chromatography high-resolution mass spectrometry", Drug Testing and Analysis, Published online in Wiley Online Library, DOI 10.1002/dta.1663, Apr. 3, 2014, 1-8.

(Continued)

Primary Examiner — Galina M. Yakovleva
(74) Attorney, Agent, or Firm — Gavrilovich, Dodd & Lindsey LLP

(57) ABSTRACT

An immunoassay method for detecting and determining adamantane substituted indazole and indole synthetic cannabinoids is described. Also described are components for use in implementing the method, namely, antibodies, detection agents, solid state devices and kits as well as immunogens used to raise the antibodies.

8 Claims, 3 Drawing Sheets

(56) References Cited

OTHER PUBLICATIONS

Figure 1:
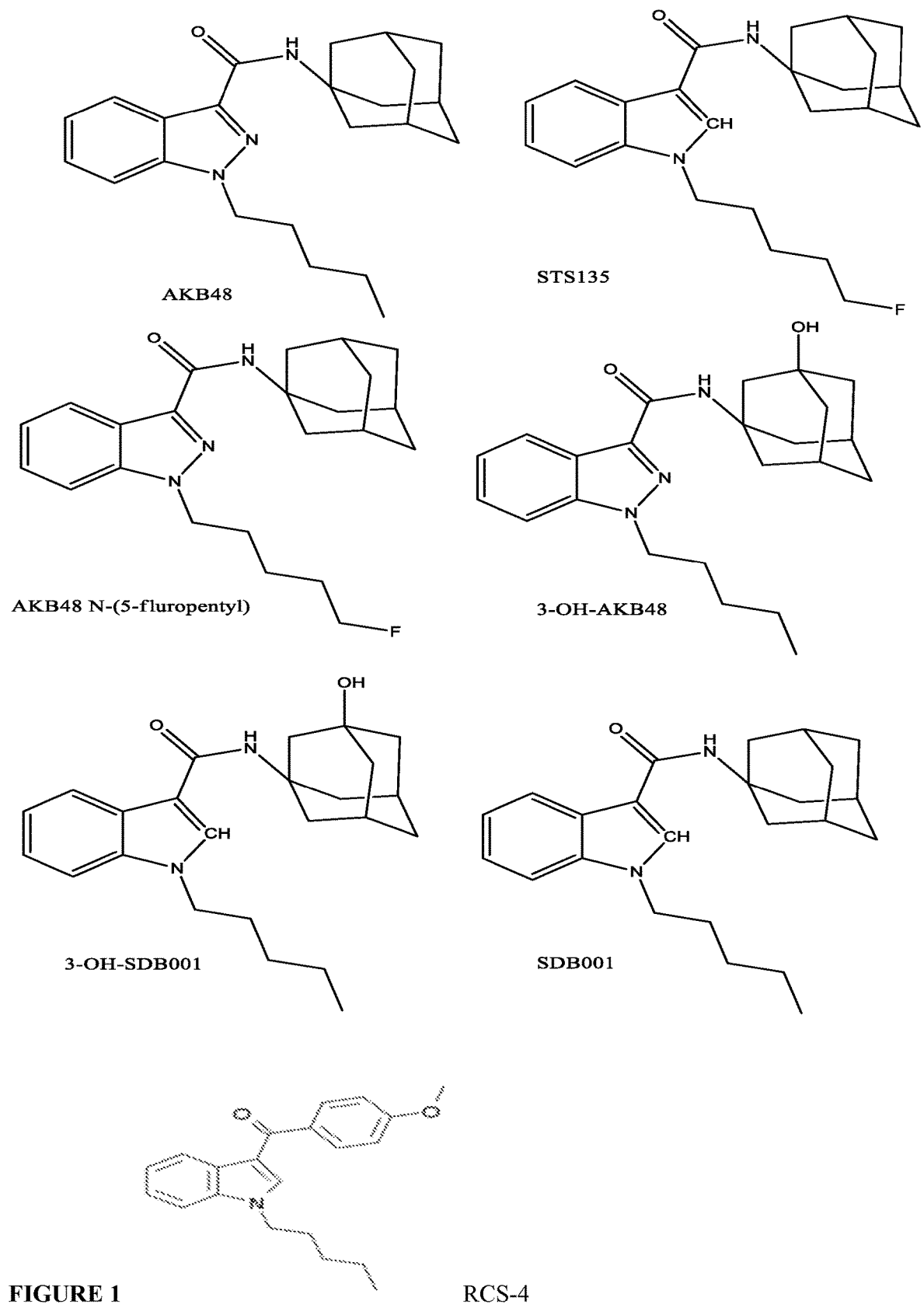

Su, et al., "Characterization of the In Vitro and In Vivo Metabolism and Disposition and Cytochrome P450 Inhibition/Induction Profile of Saxagliptin in Human", Drug Metabolism and Disposition, vol. 40, No. 7, Apr. 10, 2012, 1345-1356.

Uchiyama, et al., "Identification of two new-type synthetic cannabinoids, N-(l-adamantyl)-1-pentyl-IH-indole-3-carboxamide (APICA) and N-(l-adamantyl)-1-pentyl-IH-indazole-3-carboxamide (APINACA), and detection of five synthetic cannabinoids, AM-1220, AM-2233, AM-1241, CB-13", Forensic Toxicol (2012) 30, Apr. 11, 2012, 114-125.

Xu, et al., "Prevention and reversal of cardiac hypertrophy by soluble epoxide hydrolase inhibitors", PNAS, vol. 103, No. 49, Dec. 5, 2006, 18733-18738.

\* cited by examiner

Tracer

Immunogen

IMMUNOASSAY FOR SYNTHETIC CANNABINOIDS OF THE ADAMANTYL INDAZOLE/INDOLE-3-CARBOXAMIDE FAMILY

CROSS REFERENCE TO RELATED APPLICATIONS

This application claims the priority benefit of the earlier filing date of Great Britain Application No. 1409464.3, filed on 28 May 2014 and Great Britain Application No. 1409514.5, filed on 29 May 2014, both of which are specifically incorporated herein by reference in their entirety.

BACKGROUND

Synthetic cannabinoids (SC) are laboratory-made drugs that act upon the CB1 cannabinoid receptor mimicking the effect of the psychoactive plant derived compound $\Delta^9$-tetrahydrocannabinol. Since the first identification of SC in herbal products in 2009, new SC have proliferated as drug suppliers attempt to circumvent legislative restrictions relating to the production and use of known SC and to stay one step ahead of the forensic system by producing analogues with analytically uncharacterised chemical structures. Previously introduced SC include the naphthoylindoles, phenylacetylindoles, cyclopropanoylindoles and naphthoylpyrroles. Among the new wave of SC are indazole and indole 3-carboxamides with adamantyl and alkyl substituents on the N-carboxamide and 1-nitrogen atom of the heterocyclic ring, respectively (Grigoryev et al 2012 (This paper refers to AB001 and not AKB48); Uchiyama et al 2012; Amato et al 2014). Current identification of parent molecules and their metabolites is by gas chromatography-mass spectrometry (GC-MS), liquid chromatography-mass spectrometry (LC-MS) and nuclear magnetic resonance (NMR), analytical methods which require specialist staff for their operation. Immunoassays, dependent upon antibody-analyte binding, are a more practical and cheaper alternative. Competitive immunosassays are available for SC families such as naphthoylindoles and phenylacetylindoles (e.g. our EP2487155 A1) but not for the new wave of SC based on adamantyl-substituted indazole and indole 3-carboxamides.

AKB48 is N-(1-adamantyl)-1-pentyl-1H-indole-3-carboxamide.

REFERENCES

Amato J. et al 2014. Journal of Forensic Science & Criminology, 1: 1-6.
Gandhi A. S. et al 2013. AAPS Journal, 15: 1091-1098.
Gandhi A. S. et al 2014. Drug Testing and Analysis, DOI 10.1002/dta.1662.
Grigoryev A. et al 2012. Drug Testing and Analysis, 4: 519-24.
Holm N. B. et al 2014. Drug Testing and Analysis, DOI 10.1002/dta.1663.
Su H. et al 2012. Drug Metabolism and Disposition, 40: 1345-1356.
Uchiyama N. et al 2012. Forensic Toxicology, 30: 114-125.
Uchiyama N. et al 2013. Forensic Science International 227: 21-32.
Xu D. et al 2006. PNAS, 103: 18733-18738.

FIGURES

Figure 2:
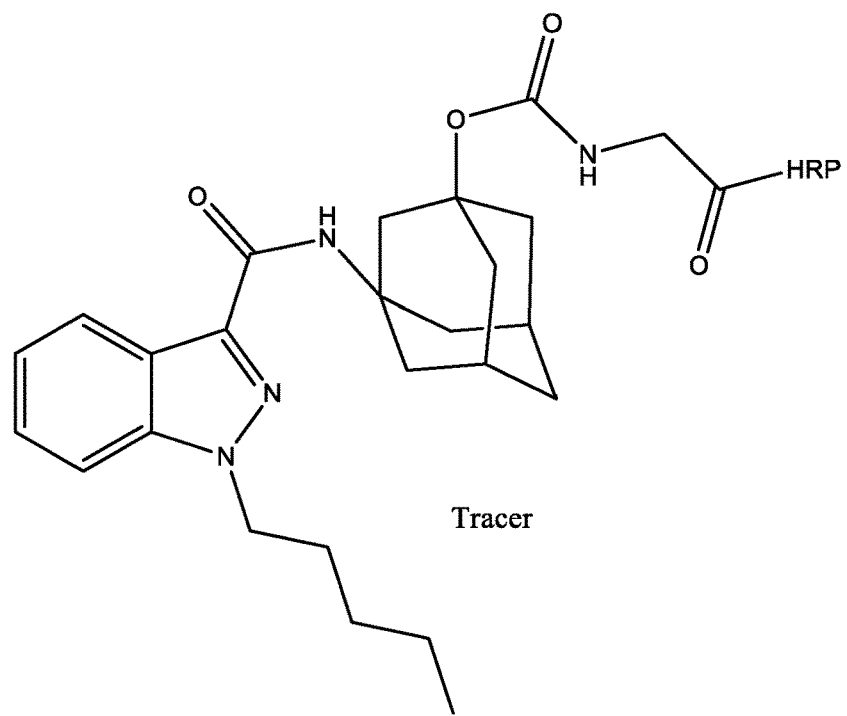
Figure 2:
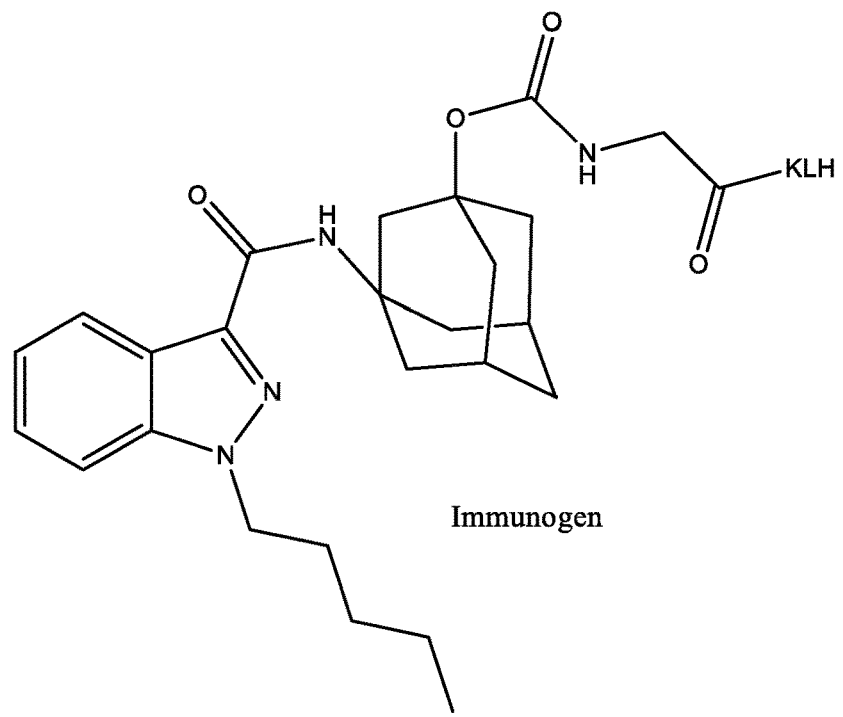
Figure 3:
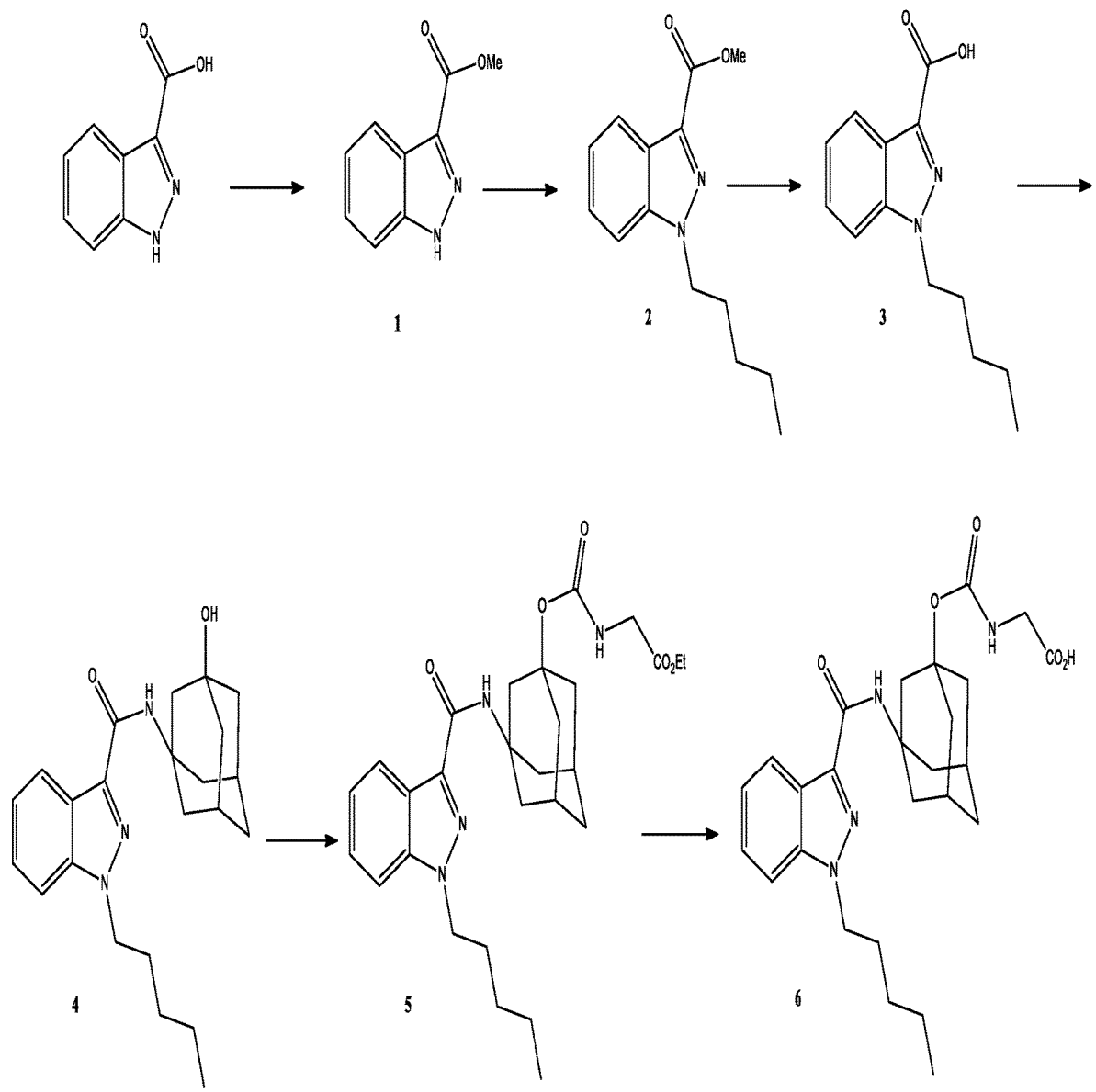

FIG. 1 Synthetic Cannabinoids of the adamantyl indazole/indole-3-carboxamide family and RCS-4.
FIG. 2 Tracer and immunogen.
FIG. 3 Synthetic route to the precursor molecule used for immunogen synthesis.

SUMMARY OF THE INVENTION

The invention describes an immunoassay method for the detection of synthetic cannabinoids of N-alkylindazole and N-alkylindole families incorporating an adamantylaminocarbonyl substituent. The invention also describes antibodies and immunogens used to raise the antibodies and kits. Unexpectedly, the antibodies bind to a small group of structurally diverse molecules. These molecules are indazoles and indole 3-carboxamides incorporating substituted and unsubstituted alkyl and substituted and unsubstituted adamantyl groups, and surprisingly, the antibodies of the invention have a marked preferential binding for 3-OH-AKB48.

DETAILED DESCRIPTION OF THE INVENTION

The invention describes an immunoassay method of detecting or determining compounds of Structure I

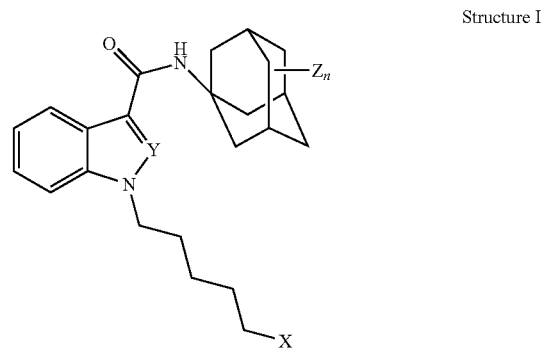

Structure I wherein X is H or a halogen; Y is N or CH; Z is H or OH; and, when Z is OH, n is an integer from 1 to 3, comprising contacting a solution or an in vitro sample taken from an individual suspected of containing compounds of Structure I with an antibody which binds to one or more epitopes of Structure I; and one or more detecting agents;

measuring the signal produced by the one or more detecting agents; and deducing from a calibrator the presence of, or amount of, compounds of Structure I.

Optionally, the invention describes a method for detecting or determining compounds of Structure I'

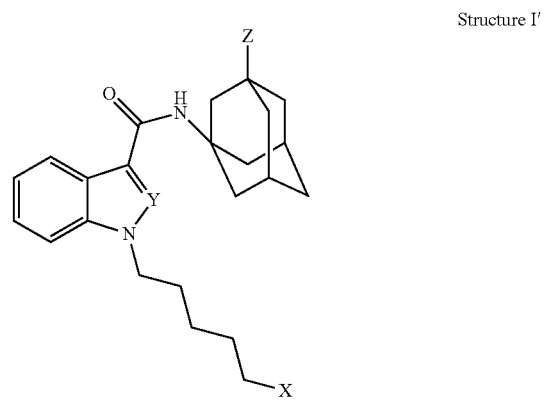

Structure I' wherein X is H or halogen; Y is N or CH; Z is H or OH, comprising contacting a solution or an in vitro sample taken from an individual suspected of containing compounds of Structure I' with an antibody which binds to one or more epitopes of Structure I; and one or more detecting agents;

measuring the signal produced by the one or more detecting agents; and deducing from a calibrator the presence of, or amount of, compounds of Structure I'.

By 'detecting' is meant qualitatively analysing for the presence or absence of a substance. By 'determining' is meant quantitatively analysing for the amount of a substance present.

In preferred embodiments, Structure I or Structure I' has
i. Y=N, Z=H and X=H or halogen or
ii. Y=CH, Z=OH and X=H or halogen or
iii. Y=N, Z=OH and X=H or halogen or
iv. Y=CH, Z=H and X=H or halogen,
of which structures of options i to iii above are preferred.

When X is halogen, halogen can be F, Cl, Br or I but is preferably F.

When Y=N, Z=H and X=H, the substance is AKB48. When Y=N, Z=H and X=halogen and the halogen is F, the substance is N-(5-fluoropentyl)-AKB48.

When Y=CH, Z=OH and X=H, the substance is 3-OH-SDB001. When Y=CH, Z=OH and X=halogen, the substance is N-(5-halopentyl)-3-OH-SDB001.

When Y=N, Z=OH and X=H, the substance is 3-OH-AKB48. When Y=N, Z=OH and X=halogen, the substance is N-(5-halopentyl)-3-OH-AKB48.

When Y=CH, Z=H and X=H, the substance is SDB001. When Y=CH, Z=H and X=halogen, the substance is N-(5-halopentyl)-SDB001; and, when Y=CH, Z=H and X=F, the substance is N-(5-fluoropentyl)-SDB001 or STS135.

Compounds of Structure I include AKB48, 3-OH-AKB48, N-(5-fluoropentyl)-AKB48 and 3-OH-SDB001 (FIG. 1).

The term 'calibrator' is well known in the art and refers to a reference value or values, the reference being a substance which enables a threshold concentration or the exact or calibrator equivalent amount of analyte(s) to be determined. The determination of an exact or calibrator equivalent amount of analyte(s) usually requires the construction of a calibration curve (also known as a standard curve). The number of calibrator points can vary, but is usually from 5 to 9. To enable a practical assay for clinical/commercial use, the binding of the antibody to the analyte(s) must be such that the concentration at which the analytes are detected or determined is at an acceptable level.

The detecting agent (also known as a tracer) is the substance which emits a detectable signal and comprises a moiety of similar structure to a target analyte conjugated, by way of a crosslinker, to a labelling agent, that is able to bind to one of the antibodies of the invention; its structure preferably comprises a 3-(1-adamantylaminocarbonyl) N-alkylindazole or N-alkylindole. The labelling agent, a component which is standard in the art, is selected from an enzyme, a luminescent substance, a radioactive substance, or a mixture thereof. Preferably, the labelling agent is an enzyme, preferably a peroxidase, most preferably horseradish peroxidase (HRP). Alternatively, or additionally, the luminescent substance may be a bioluminescent, chemiluminescent or fluorescent material.

Thus in a preferred embodiment the immunoassay method of the invention comprises a detecting agent of Structure II

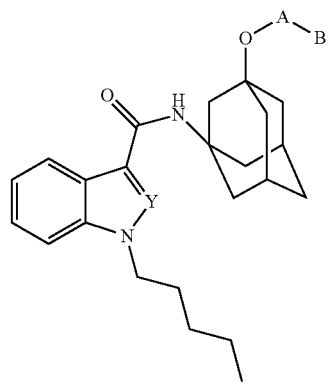

Structure II wherein A is a crosslinking group and B is a detectable label (labelling agent) and wherein Y is N or CH, preferably N.

In a preferred embodiment, the crosslinking group (A) is a $C_{1-10}$, preferably a $C_{1-5}$, substituted or unsubstituted straight chain alkylene moiety or an arylene moiety. The substituents of the alkylene chain can either be incorporated off, within or at the end of the chain. Usually the substituents will be functional groups at the end of the chain which have participated in chemical bonding in order to form a link between the adamantyl substituted indazole/indole carboxamide and the detectable label. For example, —C(O)— and —C(O)—NH— represent possible alkylene chain end substituents (at either, or both, ends of the straight chain alkylene moiety) which, prior to incorporation into Structure II, could have been part of an ester or isocyanate functional group, respectively.

The detecting agent is the compound that can be detected and comprises a moiety of similar structure to a molecule to be detected that is able to bind to one of the antibodies of the invention. An exemplary detecting agent is one in which X is —C(O)—NH—$CH_2$—C(O)— and Y is horseradish peroxidase (HRP). The preparation of this tracer is described in Example 10; equally applicable crosslinking groups and detectable labels for detecting agents of the invention are described in the General Methods, Examples and Results section. For the purposes of the invention, the patient sample to be used for in vitro analysis can be any suitable biological substance such as hair (suitably prepared for analysis) but is preferably whole blood, serum, plasma or saliva and most preferably urine.

The invention also describes an antibody which binds to an epitope of Structure C:

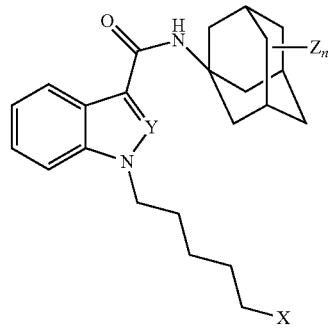

Structure C in which
i) Y is N, Z is H and X is H or halogen,
ii) Y is CH, Z is OH, n is an integer from 1 to 3 (optionally 1), and X is H or halogen or
iii) Y is N, Z is OH, n is an integer from 1 to 3 (optionally 1), and X is H or halogen or
iv) Y=CH, Z=H and X=H or halogen,
of which structures of options i to iii above are preferred.
Preferably the antibody binds to an epitope of Structure C'

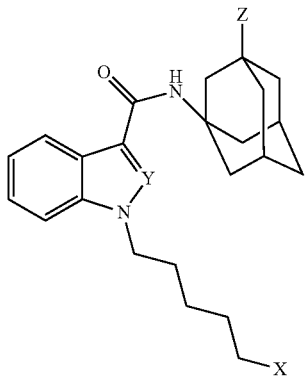

Structure C' in which
i) Y is N, Z is H and X is H or halogen,
ii) Y is CH, Z is OH and X is H or halogen,
iii) Y is N, Z is OH and X is H or halogen and
iv) Y=CH, Z=H and X=H or halogen,
of which structures of options i to iii above are preferred.
Halogen can be F, Cl, Br and I, but is preferably F.

The antibody can bind to, amongst others, AKB48, STS135, AKB48 N-(5-fluoropentyl), 3-OH-AKB48, SDB001 and 3-OH-SDB001 (FIG. 1). It will be recognised by the skilled person that the phrase 'an antibody which binds to an epitope of Structure X or Structure X' implies if only one molecule with one or more bindable epitopes, for example AKB48, exists in the sample or solution being analysed then only AKB48 will be bound by the antibody whereas, if two molecules were present each with one or more bindable epitopes, for example AKB48 and AKB48 N-(5-fluoropentyl), then both these two molecules would be bound by the antibody.

Preferably, the antibody substantially binds to 3-OH-AKB48 and is cross-reactive to AKB48, STS135, AKB48 N-(5-fluoropentyl), SDB001 and 3-OH-SDB001. 'Substantially binds to', in the current context, means having the greatest cross-reactivity to that substance.

All cross-reactivity are measured herein under the experimental conditions of Example 12 and compared to 100% for AKB48.

Optionally, or additionally, the antibody does not bind to substances not comprising an adamantyl ring. "Does not bind", in the current context, means having a cross-reactivity of less than 2% when measured under the experimental conditions of Example 12 when compared to 100% cross-reactivity for AKB48 when measured under the same conditions.

There are several parameters that can be used to compare the relative degree of binding to an antibody of different analytes including the lowest limit of detection, the lowest limit of quantification and the $IC_{50}$.

The $IC_{50}$ is determined using a competitive assay (see Example 12 of the General Method, Examples and Results and Tables 1 and 2) and can be used to derive analyte cross-reactivities.

To enable an assay to be effectively applied in the field, an $IC_{50}$ of less than or about 20 ng/ml, preferably less than or about 10 ng/ml, most preferably less than or about 5 ng/ml, for any individual analyte is preferred when measured under the experimental conditions of Example 12.

Another embodiment of the invention describes the antibody-analyte binding as defined by the $IC_{50}$, in which 3-OH-AKB48 has an $IC_{50}$ of less than or about 5 ng/ml, preferably less than or about 1 ng/ml, even more preferably less than or about 0.2 ng/ml. A typical $IC_{50}$ for 3-OH-AKB48 is in the range of 0.10-1.00 ng/ml, preferably in the range of 0.10-0.50 ng/ml.

Alternatively or additionally, the $IC_{50}$'s of each of AKB48, N-(5-fluoropentyl)-AKB48 and 3-OH-SDB001 are in the range of 1.00-15.00 ng/ml, preferably 1.00-10.00 ng/ml, most preferably 1.00-5.00 ng/ml.

In contrast, the $IC_{50}$'s of each of STS135 and SDB001 are in the range of 20.00 to 60.00 ng/ml.

Given the $IC_{50}$ of various analytes, their cross-reactivities, often represented as relative percentages, can be calculated.

In a further embodiment, the invention describes an antibody that has 100% cross-reactivity (CR) to AKB48 and at least or about 1100% CR to 3-OH-AKB48, at least or about 95% CR to AKB48 N-(5-fluoropentyl), at least or about 45% CR to 3-OH-SDB001; the antibody may also have at least or about 8% CR to STS135 and at least or about 4% CR to SDB001.

If a polyclonal antibody possesses the required specificity and sensitivity, for example, it binds a single analyte within the desirable detection range of the assay, development of monoclonal antibody may be unnecessary.

Alternatively or additionally, antibodies of the invention have a cross-reactivity of >500% and less than 1,500% for 3-OH-AKB48 when compared to 100% cross-reactivity for AKB48 when measured under the same conditions of Example 12.

Alternatively or additionally, antibodies of the present invention have a cross-reactivity of >80% and <120% for the N-5 fluoropentyl derivative of AKB48 when compared to 100% cross-reactivity for AKB48 when measured under the same conditions of Example 12.

Alternatively or additionally, antibodies of the present invention have a cross-reactivity of >30% and <70% for 3-OH-SDB001 when compared to 100% cross-reactivity for AKB48 when measured under the same conditions of Example 12.

Alternatively or additionally, antibodies of the present invention have a cross-reactivity of >2% and <20% for one or both of STS135 and SDB001 when compared to 100% cross-reactivity for AKB48 when measured under the same conditions of Example 12.

Alternatively, a polyclonal or monoclonal antibody that bind to several different analytes might be desirable; in the context of the current invention, due to the number of synthetic cannabinoids (SC) in the families of interest, antibodies that bind several analytes are preferred. The antibody is able to be further characterised in being derived from an immunogen of Structure III. Thus the invention also describes an immunogen Structure III

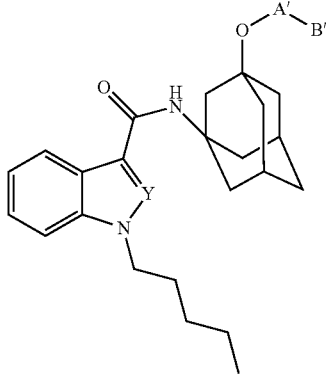

wherein A' is a crosslinking group and B' is an antigenicity-conferring carrier material and wherein Y is N or CH, preferably N.

Preferably, A' is a $C_{1-10}$, preferably a $C_{1-5}$ substituted or unsubstituted straight chain alkylene moiety or an arylene moiety. The substituents of the alkylene chain can either be incorporated off, within or at the end of the chain. Usually the substituents will be functional groups at the end of the chain which have participated in chemical bonding in order to form a link between the adamantyl substituted indazole/indole carboxamide and the antigenicity-conferring carrier material. For example, —C(O)— and —C(O)—NH— represent possible alkylene chain end substituents (at either, or both, ends of the straight chain alkylene moiety) which, prior to incorporation into Structure III, could have been part of an ester or isocyanate functional group, respectively.

An exemplary immunogen is one in which X is —C(O)—NH—CH$_2$—C(O)— and Y is keyhole limpet hemocyanin (KLH)—the preparation of this immunogen is described in Example 9 (see FIG. 2 for structure); equally applicable crosslinking groups and antigenicity-conferring carrier materials for immunogens of Structure III of the invention are described in the General Methods, Examples and Results section.

A further aspect of the invention is a compound of Structure IV

Structure IV

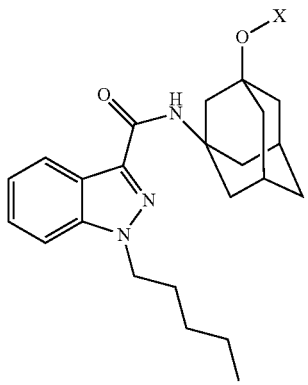

wherein X is H; —C(O)—NH—CH$_2$—CO$_2$Y; or —C(O)—NH—CH$_2$—CO$_2$H, and Y is $C_1$-$C_6$ alkyl, preferably methyl, ethyl, n-propyl, i-propyl or n-butyl.

A method of synthesizing a compound of Structure IV in which X is H comprises i) esterifying 1H-indazole-3-carboxylic acid to form 1H-indazole-3-carboxylate ester
ii) pentylating the 1-N atom of 1H-indazole-3-carboxylate ester to form 1-pentyl-indazole-3-carboxylate ester
iii) hydrolysing 1-pentyl-1H-indazole-3-carboxylate ester to form 1-pentyl-1H-indazole-3-carboxylic acid
iv) reacting 1-pentyl-indazole-3-carboxylic acid with 3-amino-1-adamantanol to give (3-hydroxy-1-adamantyl) 1-pentylindazole-3-carboxamide (3-OH-AKB48).

A method of synthesizing a compound of Structure IV in which X is —C(O)—NH—CH$_2$—CO$_2$-alkyl comprises undertaking steps i) to iv) described above and reacting (3-hydroxy-1-adamantanyl) 1-pentyl-1H-indazole-3-carboxamide with alkyl isocyanatoacetate to give alkyl 2-[-3-(1-pentyl-1H-indazole-3-carboxamido)adamantan-1-yloxycarbonylamino]acetate, wherein alkyl is $C_1$-$C_6$ alkyl, preferably methyl, ethyl, n-propyl, i-propyl or n-butyl.

A method of synthesizing a compound of Structure IV in which X is C(O)—NH—CH$_2$—CO$_2$—H comprises undertaking steps i) to iv) as described previously, reacting the product with an alkyl isocyanatoacetate as described above and hydrolysing to give 2-[-3-(1-pentyl-1H-indazole-3-carboxamido)adamantan-1-yloxycarbonylamino]ethanoic acid. The conditions used to conduct these synthetic procedures for molecules of Structure IV are described in the Examples section. The skilled synthetic chemist is aware that the described experimental conditions in the Examples section are amenable to a degree of flexibility without affecting the nature of the end product.

In the immunodiagnostic field, there are several alternative immunoassay formats that could incorporate the antibodies of the invention either in solution or tethered, for example covalently bonded or electrostatically 'non-bonded' through Van der Waal's forces, to a solid state device such as beads, glass/plastic slides, ceramic chips. A chip is a small, planar solid state device usually with a flat surface (although it may incorporate wells or columns for supporting the antibodies or analytes), with or without walls, capable of supporting the antibodies or analytes. A preferred solid state device onto which the antibodies of the invention are covalently bonded is a chip, preferably a ceramic chip; the word 'biochip' can be used to refer to a chip with antibodies attached. The chip can be integral to or placed into a device with walls. Such a walled device can aid in the retention of added sample or solution. Therefore, another aspect of the invention is a solid state device, preferably a biochip which is preferably ceramic, which supports one or more antibodies of the invention. The solid state device can also support other antibodies which have a binding specificity which is different from the binding specificity of the antibodies of the invention. Such a support with multiple different antibodies is often described as a multianalyte array (Reference to an 'array' includes a microarray). If the method of detection is different fluorescent labels, each different fluorescent label emitting electromagnetic radiation at a unique wavelength, then the location of placement of the antibodies on the solid substrate is not critical. However, for antibodies forming part of a multianalyte array in which the detectable label is, for example, a chemiluminescent molecule, the antibodies of differing specificity must not overlap and must be located in discrete areas on the solid state device. Such a system is also referred to as a spatially addressable multianalyte array.

The invention also describes kits for detecting or determining substituted or unsubstituted adamantyl N-alkyl indazoles/indoles 3-carboxamides comprising one or more antibodies of the invention. Preferably, the kit comprises one or more antibodies derived from an immunogen of Structure III. The antibodies of the kit are preferably associated with a suitable solid state device, preferably by covalent bonding, although they may be associated through a non-bonding mechanism such as Van der Waal's forces. Although the solid state device can be of any suitable shape such as a bead, slide or chip, walled or un-walled, and of any suitable material such as silicon, glass or plastic, the solid state device is preferably a ceramic chip or microtitre plate. The kit may further include one or more calibrators and one or more tracers of the invention and optionally includes instructions for use.

General Methods, Examples and Results

Preparation of Haptens, Immunogens and Detecting Agents

In immunology, haptens are defined as substances which by themselves cannot elicit immune responses; they require chemical coupling to larger immunogenic molecules (antigenicity conferring carrier materials or 'accm'), to be capable of inducing an immune response. Appropriate accms commonly contain poly(amino acid) segments and include polypeptides, proteins and protein fragments. Illustrative examples of antigencity conferring carrier materials are keyhole limpet haemocyanin (KLH), bovine thyroglobulin (BTG), bovine serum albumin (BSA), egg ovalbumin, bovine gamma globulin or cationised BSA. Alternatively, synthetic poly(amino acids) having a sufficient number of available amino groups, such as lysine, may be employed, as may other synthetic or natural polymeric materials bearing reactive functional groups. Also, carbohydrates, yeasts or polysaccharides may be conjugated to the hapten to produce an immunogen. The haptens can also be coupled to a detectable labelling agent such as an enzyme (for example, horseradish peroxidase), a substance having fluorescent properties or a radioactive label for the preparation of detecting agents for use in the immunoassays. The fluorescent substance may be, for example, a monovalent residue of fluorescein or a derivative thereof. Conjugation of haptens can be performed using standard methods of conjugation such as mixed anhydride, EDC or succinimidyl activation of the haptens. In order to confirm that adequate conjugation of hapten to carrier material has been achieved, prior to immunisation, each immunogen is evaluated using matrix-assisted UV laser desorption/ionisation time-of-flight mass spectroscopy (MALDI-TOF MS).

General Procedure for MALDI-TOF Analysis of Immunogens

MALDI-TOF mass spectrometry was performed using a Voyager STR Biospectrometry Research Station laser-desorption mass spectrometer coupled with delayed extraction. An aliquot of each sample to be analysed was diluted in 0.1% aqueous trifluoroacetic acid (TFA) to create 1 mg/ml sample solutions. Aliquots (1 μl) were analysed using a matrix of sinapinic acid and bovine serum albumin (Fluka) was used as an external calibrant.

Preparation of Antisera

In order to generate polyclonal antisera, an immunogen of the present invention is mixed with Freund's adjuvant and the mixture is injected into a host animal, such as rabbit, sheep, mouse, guinea pig or horse. Sheep are the preferred host animal. Further injections (boosts) are made and serum is sampled for evaluation of the antibody titre. When the optimal titre has been attained, the host animal is bled to yield a suitable volume of specific antiserum. The degree of antibody purification required depends on the intended application. For many purposes, there is no requirement for purification, however, in other cases, such as where the antibody is to be immobilised on a solid support, purification steps can be taken to remove undesired material and eliminate non-specific binding.

Immunoassay Development

The process of developing an immunoassay is well known to the person skilled in the art. Briefly, for a competitive immunoassay in which the target analyte is a non-immunogenic molecule such as a hapten, the following process is conducted: antibodies are produced by immunising an animal, preferably a mammalian animal, by repeated administration of an immunogen. The serum from the immunised animal is collected when the antibody titre is sufficiently high. A detecting agent is added to a sample containing the target analyte and the raised antibodies, and the detecting agent and analyte compete for binding to the antibodies. The process may comprise fixing said serum antibodies to a solid state device such as a polystyrene support or a ceramic chip. The antibodies can be polyclonal or monoclonal using standard techniques, but the current invention makes use of polyclonal antibodies. The signal emitted in the immunoassay is proportionate to the quantity of detecting agent bound to the antibodies which in turn is inversely proportionate to the analyte concentration. The signal can be detected or quantified by comparison with a calibrator.

Example-1: Preparation of Adamantan-1-yl 1H-indazole-3-carboxamide

DIPEA (23.6 ml, 0.1382 mol) was added to a solution of indazole-3-carboxylic acid (4 g, 0.02469 mol) in DMF (50 ml) and the solution stirred at room temperature for 10 minutes. HBTU (14 g, 0.03703 mol) was added and the solution was stirred at room temperature for 3 hours. 1-Adamantanylamine (5.6 g, 0.03703 mol) was then added and the solution stirred at room temperature for 16 hours. The solvent was removed under vacuum and the residue dissolved in EtOAc (100 ml) and washed with a saturated aqueous solution of sodium bicarbonate (100 ml), water (50 ml), brine (50 ml) then dried over sodium sulphate, filtered and concentrated in vacuo. The crude residue was purified by column chromatography (Silica gel 5% MeOH in chloroform) to give Adamantan-1-yl 1H-indazole-3-carboxamide (2.47 g, 34%).

Example-2: Preparation of Methyl 1H-indazole-3-carboxylate

Sulfuric acid (18 ml) was added to a solution of indazole-3-carboxylic acid (19.3 g, 0.119 mol) in methanol and the solution was stirred at 60° C. overnight. The solvent was removed in vacuo and the residue dissolved in ethyl acetate (500 ml) and washed with water (200 ml). The aqueous layer was extracted with ethyl acetate (2×100 ml) and the combined organic layers were dried over sodium sulphate, filtered and concentrated in vacuo to give (22.76 g) of Methyl 1H-indazole-3-carboxylate as a cream coloured solid.

Example-3: Preparation of Methyl 1-pentyl-1H-indazole-3-carboxylate

Potassium tert-butoxide (7.22 g, 0.0643 mol) was added to a solution of Methyl 1H-indazole-3-carboxylate (10.3 g, 0.0585 mol) in THF (100 ml) at 0° C. and the solution stirred at 0° C. for 1 hour. Pentylbromide (11.6 ml, 0.0936 mol) was added at 0° C. and the solution was stirred at room temperature for 56 hours. The solvents were removed in vacuo and the residue dissolved in water and DCM. The separated aqueous layer was extracted with DCM (2×100 ml) and the combined organics layers were dried over sodium sulphate, filtered and concentrated in vacuo. The crude residue was purified by column chromatography on biotage (5% EtOAc in hexane) to give (7.26 g) of Methyl 1-pentyl-1H-indazole-3-carboxylate.

Example-4: Preparation of 1-Pentyl-1H-indazole-3-carboxylic acid

Sodium hydroxide (3M, 30 ml) was added to a solution of Methyl 1-pentyl-1H-indazole-3-carboxylate (7.26 g, 0.0295 mol) in methanol (100 ml) and the solution stirred at room temperature for 3 hours. The solvents were removed in vacuo and the remaining aqueous solution was extracted with diethyl ether (50 ml) and then acidifed to pH 1 using 3M HCl. The aqueous layer was extracted with EtOAc (3×100 ml) and the combined organics layers were dried over sodium sulphate, filtered and concentrated in vacuo to give (7.38 g) of 1-Pentyl-1H-indazole-3-carboxylic acid.

Example-5: Preparation of 3-OH-AKB48

DIPEA (4.2 ml, 0.02445 mol) was added to a solution of 1-Pentyl-1H-indazole-3-carboxylic acid (1.013 g, 0.004366 mol) in DMF (10 ml) and the solution was stirred at room temperature for 10 minutes. HBTU (2.48 g, 0.00655 mol) was added and the solution was stirred again at room temperature for 3 hours. 3-Amino-1-adamantanol hydrate (1.21 g, 0.00655 mol) was then added and the solution stirred at room temperature for 16 hours. The solvent was removed in vacuo and the residue dissolved in EtOAc (100 ml) and washed with a saturated aqueous solution of sodium bicarbonate (50 ml), water (50 ml) and brine, then dried over sodium sulphate, filtered and concentrated in vacuo. The crude residue was purified by column chromatography (Silica gel 30% EtOAc in hexane to give (1.29 g) of 3-OH-AKB48.

Example-6: Preparation of Ethyl 2-[3-(1-pentyl-1H-indazole-3-carboxamido)adamantan-1-yloxycarbonylamino]acetate Ethyl isocyanatoacetate (650 µl, 5.037 mmol), TEA (607 µl, 4.35 mmol) and DMAP (catalytic) were added to a solution of 3-OH-AKB48 (553 mg, 1.45 mmol) in toluene (10 ml) and the mixture stirred at 60° C. for 15 hours. The solvents were removed in vacuo and the crude residue was purified by column chromatography (Silica gel, 30% EtOAc in hexane to give (9062 mg) of Ethyl 2-[3-(1-pentyl-1H-indazole-3-carboxamido)adamantan-1-yloxocarbonylamino]acetate.

Example-7: Preparation of AKB48-3-carboxymethyl urethane

Lithium hydroxide (158 mg, 3.77 mmol) was added to a solution of Ethyl 2-[3-(1-pentyl-1H-indazole-3-carboxamido)adamantan-1-yloxocarbonylamino]acetate (962 mg, 1.885 mmol) in THF/water/MeOH (10 ml) and the solution stirred at room temperature overnight. The solvents were removed in vacuo, water (20 ml) was added and the aqueous was acidified to pH 1-2 using (1M) HCl. The aqueous solution was extracted with EtOAc (3×50 ml) and the combined organics were dried over sodium sulphate, filtered and concentrated in vacuo to give (873 mg) of AKB48-3-carboxymethyl urethane.

Example-8: Conjugation of AKB48-3-carboxymethyl urethane to BSA

DMF (1 ml) was added to a vial containing AKB-48-3-carboxymethyl urethane (30.4 mg), N-Hydroxysuccinimide (44.3 mg) and EDC hydrochloride (73.7 mg), and the mixture was incubated on the roller at room temperature for 16-20 hours. This solution was added dropwise to a solution of BSA (100 mg) in 10 mL of Phosphate Buffered Saline, pH8.0. The resulting solution was incubated on the roller at room temperature overnight. Excess hapten was removed by dialysis at 2-8° C. against Phosphate Buffered Saline, pH 7.2. MALDI results showed 16.1 molecule of AKB48-3-carboxymethyl urethane had been conjugated to one molecule of BSA.

Example-9: Conjugation of AKB48-3-carboxymethyl urethane to KLH

DMF (1 ml) was added to a vial containing AKB48-3-carboxymethyl urethane (30.4 mg), N-Hydroxysuccinimide (44.3 mg) and EDC hydrochloride (73.7 mg), and the mixture was incubated on the roller at room temperature for 16-20 hours. This solution was added dropwise to a solution of KLH (100 mg) in 10 mL of Phosphate Buffered Saline, pH8.0. The resulting solution was incubated on the roller at room temperature overnight. Excess hapten was removed by dialysis at 2-8° C. against Phosphate Buffered Saline, pH 7.2.

Example-10: Conjugation of AKB48-3-carboxymethyl urethane to HRP

AKB48-3-carboxymethyl urethane (3.0 mg) was dissolved in DMF (0.3 mL) and the resulting solution was added to N-Hydroxysuccinimide (1 mg), and pipet up and down until dissolved (this should take no longer than 30 seconds). The resulting solution was added to EDC hydrochloride (1.5 mg), and the mixture was incubated on the roller at room temperature for 2 hours. This solution was added dropwise to a solution of HRP (20 mg) in 1.8 ml of Phosphate Buffered Saline, pH8.0. The resulting solution was incubated on the roller at room temperature for 16-20 hours. Keep the solution darkened. Excess hapten was removed with PD-10 column (Pharmacia), pre-equilibrated with Phosphate Buffered Saline, pH 7.2, followed by dialysis at 2-8° C. against Phosphate Buffered Saline, pH 7.2.

Example-11: Preparation of Antisera

Pre-immunization blood samples are collected from young adult, female, Texel sheep. In order to generate polyclonal antisera, 2 mgs of the immunogen (Example 9) is prepared in PBS, mixed at a ratio of 50% immunogen in PBS to 50% Freund's Complete adjuvant (Sigma, Product Number F5881) and emulsified by repeatedly passing the mixture through a tip on the end of a 1 ml syringe, until it reaches the required semi-solid consistency. 1 ml of the emulsified mixture is injected intramuscularly into each host animal (sheep) as the primary immunisation dose. Further injections (boosts) are prepared (1 mg of immunogen is prepared in PBS and mixed at a ratio of 50% Immunogen in PBS/50% Freunds Incomplete adjuvant, Sigma, Product Number—

F5506). Boost injections are delivered intramuscularly at monthly intervals, 1 ml per animal. Serum is sampled monthly by collection of whole blood from the jugular vein for evaluation of the antibody titre. The degree of antibody purification required depends on the intended application. For many purposes, there is no requirement for purification of the serum, however, in other cases, such as where the antibody is to be immobilised on a solid support, purification steps (such as caprylic acid/ammonium sulphate precipitation) can be taken to remove undesired material and eliminate non-specific binding.

Example-12: $IC_{50}$ Derivation Through Competitive Immunoassay

IgG is extracted from the antisera and immobilised on a 96 well ELISA plate (coated for 2 hours at +37° C. at 10 ug/ml in a Phosphate Buffered Saline pH7.2). Unbound material is removed by washing with Tris Buffered Saline (TBS) containing tween (3×50 ml) over 10 minutes. Standard AKB48 is added at the concentrations quoted in Table 1 (FIG. 2) at 1/140 k in a dilution buffer. After incubation (60 mins) at +15 to +25° C. to allow a competition reaction to take place, the microtitre plate is washed with TBS containing Tween™ to remove excess reagents. The enzyme substrate 5,5'-tetramethylbenzidine (125 µl) is added (Kem-en-Tec Cat. No. 4800). After a 20 minute incubation period to allow maximum colour development, the colour reaction is stopped by the addition of sulphuric acid (0.2M, 120 µl). This produces a colour change from blue to yellow, and the absorbances are read at 450 nm. A standard curve is then constructed and the $IC_{50}$ calculated as the AKB48 concentration which produces 50% inhibition of maximal signal. This process was repeated for synthetic cannabinoid members as stated in Table 2 to assess cross-reactivity.

TABLE 1

Data generated from a competitive immunoassay for AKB48 using an antibody derived from Immunogen of Example 9 and Tracer 1 of Example 10 (each shown in FIG. 2)

| AKB48 concentration (ng/ml) | Average OD ($A_{450}$) | % $B/B_0$ |
| --- | --- | --- |
| 0 | 1.672 | 100 |
| 0.25 | 1.470 | 88 |
| 0.74 | 1.159 | 69 |
| 2.22 | 0.835 | 50 |
| 6.67 | 0.434 | 26 |
| 20.00 | 0.206 | 12 |

$IC_{50}$ = 2.22 ng/ml
$A_{450}$ = absorbance at 450 nm
B = absorbance at 450 nm at x ng/ml AKB48 concentration
$B_0$ = absorbance at 450 nm at 0 ng/ml AKB48 concentration
Percentage $B/B_0$ = $(B/B_0) \times 100$
$IC_{50}$ = AKB48 concentration which produces 50% inhibition of maximal signal The cross-reactivity (CR) was calculated using the equation below. All calculations were based upon binding and displacement at the 50% of maximum OD (optical density) binding point. The maximum OD is the signal generated using tracer alone and 50% displacement (inhibition) corresponds to the $IC_{50}$.

% CR=(OD without cross-reactant−OD with cross-reactant)×100 where the cross-reactant is a single, individual synthetic cannabinoid.

The extent of antibody binding to synthetic cannabinoids of various families was assessed (Table 2). For the cross-reactants with $IC_{50}$ values, standard curves were derived for each analyte (as per AKB48 and Table 1). For the remaining analytes which did not cross-react, the single cross-reactant had <1.00% CR at 300 ng/ml. In all cases, the cross-reactivity set out in Table 2 was measured using an antibody derived from the immunogen of Example 9 and Tracer 1 of Example 10.

TABLE 2

Synthetic cannabinoids tested for their cross-reactivity ($IC_{50}$ values in brackets for the first seven substances, generated as per AKB48 and Table 1).

| CROSS-REACTANT | % CROSS-REACTIVITY ($IC_{50}$ ng/ml) |
| --- | --- |
| 3-OH-AKB48 | 1163.53 (0.18) |
| AKB48 | 100.00 (2.08) |
| AKB48 N-(5-fluoropentyl) | 98.90 (2.10) |
| 3-OH-SDB001 | 47.30 (4.40) |
| STS135 | 8.41 (24.76) |
| SDB001 | 4.07 (52.00) |
| RCS-4 | 1.67 (124.55) |
| JWH-018 | <1.00 |
| PB-22 | <1.00 |
| PB-22 3-Carboxyindole metabolite | <1.00 |
| AB Pinaca | <1.00 |
| AKB48 N-Pentanoic acid (LK1461) | <1.00 |
| SDB-001 N-Pentanoic acid (LK1404) | <1.00 |
| AM-1248 | <1.00 |
| 3-Carboxyindole metabolite of BB-22 | <1.00 |
| BB-22 | <1.00 |
| 5-fluoro PB-22 | <1.00 |
| 3-carboxyindole of 5-fluoro PB-22 | <1.00 |
| AB001 N-Pentanoic Acid | <1.00 |
| AB001 N-Pentanol | <1.00 |
| N-Desalkyl AB001 | <1.00 |
| UR-144 | <1.00 |
| XLR-11 | <1.00 |
| UR-144 N Pentanoic acid | <1.00 |
| A-7969260 | <1.00 |
| A-834735 | <1.00 |
| JWH-203 | <1.00 |
| AM-694 | <1.00 |
| JWH-200 | <1.00 |
| JWH-073 | <1.00 |
| JWH-022 | <1.00 |
| JWH-210 | <1.00 |
| AM2232 | <1.00 |
| JWH-019 | <1.00 |
| JWH-015 | <1.00 |
| AM-2201 | <1.00 |
| JWH-007 | <1.00 |
| JWH-398 | <1.00 |
| JWH-081 | <1.00 |
| RCS-8 | <1.00 |
| JWH-018 N-Pentanoic acid | <1.00 |
| JWH-018 N-(5-Hydroxypentyl) | <1.00 |
| JWH-250 N-(5-Carboxypentyl) | <1.00 |
| JWH-250 N-(5-Hydroxypentyl) | <1.00 |
| AM-2201 N-(4-Hydroxypentyl) | <1.00 |
| AM-2201 6-Hydroxyindole | <1.00 |
| JWH-018 4-Hydroxyindole | <1.00 |
| JWH-018 5-Hydroxyindole | <1.00 |
| JWH-018 6-Hydroxyindole | <1.00 |
| JWH-073 4-Hydroxyindole | <1.00 |
| JWH-073 5-Hydroxyindole | <1.00 |

Tables 1 and 2 highlight that, in order to be able to bind to the antibodies of the invention and enable an assay of sufficient sensitivity (for example, in an $IC_{50}$ in a range of 0.1 to 5 ng/ml), an analyte must incorporate the structural components adamantan-1-yl N-(alkyl)indazole-3-carboxamide or 3-hydroxyadamantan-1-yl N-(alkyl)indole-3-carboxamide, the alkyl group preferably being pentyl optionally substituted at the terminal C-atom by a halogen group; it is likely that a butyl group replacing pentyl would have similar antibody binding properties. If the SC comprises indole without a 3-OH substituent on the adamantyl ring, antibody binding is reduced (see Table 2 values of SDB001 and 3-OH-SDB001).

Surprisingly, the antibody of the invention shows great affinity for 3-OH-AKB48 enabling an assay of exceptional sensitivity ($IC_{50}$=0.18 ng/ml). Detection and determination of SC for toxicological applications requires consideration of parent molecule metabolism—a rapidly metabolised parent molecule requires analytical methods that are able to detect metabolites in order to detect drug consumption over a greater period of time. Indazole and indole 3-carboxamides with adamantyl and alkyl substituents are known to rapidly metabolise to several products, including adamantyl mono-hydroxylated metabolites (Grigoryev 2013; Gandhi 2013; Gandhi 2014; Holm 2014). Although the point of attachment of mono-hydroxylated AKB48 metabolites have not been confirmed, studies on the in vivo metabolism of adamantyl-containing xenobiotics in mammals, including humans, strongly indicate that 3-hydroxyadamantyl is a major metabolite (Su et al 2012; Xu et al 2006).

AB001 is shown below:

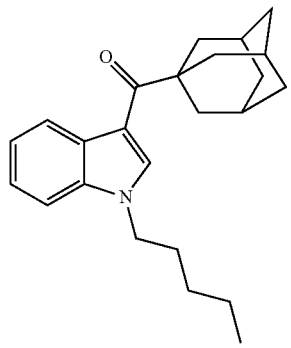 [SMILES: CCCCCn1cc(C(=O)C23CC4CC(CC(C4)C2)C3)c2ccccc21]

The AB001 family incorporates a ketone group between the heterocyclic ring system and the adamantyl ring of AKB48, as opposed to a carboxamide group. AB001 N-pentanoic acid and AB001 N-pentanol comprise AB001 in which the terminal methyl is replaced by a COOH group and in which an OH is added to the terminal methyl group, respectively.

The antibodies of the present invention do not bind to AB001 N-pentanoic acid and AB001 N-pentanol. It is hypothesized that the additional molecular length and rotational flexibility that the carboxamide group imparts, as well as, the powerful epitopic potential of the —NH— atom through hydrogen bonding explain why these derivatives of AB001 ds not bind to the antibodies of the invention JWH-018 shares a 1-pentylindol-3-ylmethanone with AKB48, but incorporates a ketone group between the indole ring system and the other ring, in this case, a naphthalene ring. JWH-018 N-Pentanoic acid and JWH-018 N-(5-Hydroxypentyl) differ from JWH-018 in the identity of the N-side chain. JWH-018 4-Hydroxyindole, JWH-018 5-Hydroxyindole and JWH-018 6-Hydroxyindole differ from JWH-018 in comprising a further OH on the indole ring. JWH-210 differs from JWH-018 in having a 4-ethyl naphthalene ring. JWH-398 differs from JWH-018 in having a 4-chloro naphthalene ring. JWH-081 differs from JWH-018 in having a 4-methoxy naphthalene ring. JWH-022 differs from JWH-018 in having an N-4-pentenyl side chain. AM2232 differs from JWH-018 in having an N-pentane nitrile side chain. AM-2201 is identical with JWH-018 other than a terminal F on the N-pentyl side chain. AM-2201 N-(4-Hydroxypentyl) differs from AM-2201 in the identity of its N-side chain. AM-2201 6-Hydroxyindole differs from AM-2201 in having an OH on the indole group. JWH-019 differs from JWH-018 in having an N-hexyl side chain. JWH-015 differs from JWH-018 in having an N-propyl side chain and there is a methyl substituent on the 2-position of the indole. JWH-007 differs from JWH-018 in having a methyl substituent on the 2-position of the indole.

It is hypothesized that the additional molecular length and rotational flexibility that the carboxamide group imparts, as well as, the powerful epitopic potential of the —NH— atom through hydrogen bonding, together with the replacement of the adamantyl regroup with a naphthalene ring, explain why JWH-018 and the derivatives mentioned above do not bind to the antibodies of the invention.

RCS-4 shares a 1-pentylindol-3-yl methanone with AKB48, but incorporates a ketone group between the indole ring system and the other ring—in this case, a phenyl ring. It is hypothesised that the additional molecular length and rotational flexibility that the carboxamide group imparts, as well as, the powerful epitopic potential of the —NH— atom through hydrogen bonding and the absence of the adamantyl group would explain why RCS-4 does not bind to the antibodies of the invention.

RCS-8 shares an indol-3-yl methanone with AKB48 and incorporates a carboxamide group between the indole ring system and the other ring—in this case a 2-methoxyphenyl ring. RCS-8 also has a 2-cyclohexyl-ethyl substituent on the N of the indole. The absence of the adamantyl group would explain why RCS-8 does not bind to the antibodies of the invention.

PB-22 shares a 1-pentylindol-3-yl methanone with AKB48 and incorporates a carboxamide group between the indole ring system and the other ring—in this case a quinoline. The absence of the adamantyl group would explain why PB-22 does not bind to the antibodies of the invention.

AB Pinaca shares a 1-pentylindazol-3-yl methanone with AKB48 and incorporates a carboxamide group between the indole ring system and the rest of the molecule. The absence of the adamantyl group would explain why AB Pinaca does not bind to the antibodies of the invention.

AKB48 N-Pentanoic acid and SDB-001 N-Pentanoic acid differ from AKB48 and SDB-001, respectively, in the N-side chain. The presence of a carboxylic acid at the end of the side chain would explain why these substances do not bind to the antibodies of the invention.

AM-1248 shares an indol-3-yl methanone with AKB48, but incorporates a ketone group between the indole ring system and the adamantyl group. AM-1248 also differs from AKB48 in the N-side chain including a piperidine. It is hypothesised that the additional molecular length and rotational flexibility that the carboxamide group imparts, as well as, the powerful epitopic potential of the —NH— atom through hydrogen bonding and the piperidine substitution on the N-pentyl group would explain why AM-1248 does not bind to the antibodies of the invention.

BB-22 shares an indol-3-yl methanone with AKB48, but incorporates an ester group between the indole ring system and the other ring, in this case, a quinolone. BB-22 also differs from AKB48 by having an N-methyl cyclohexyl group.

UR-144 shares a 1-pentylindol-3-yl methanone with AKB48, but incorporates a ketone group between the indole ring system and the other ring, in this case, a tetramethyl cyclopropane. XLR-11 shares a 1-pentylindol-3-yl methanone with AKB48, but incorporates a ketone group between the indole ring system and the other ring, in this case, a tetramethyl cyclopropane. XLR-11 differs from UR-144 in having a 5-fluoro substitution on the pentyl side chain, permitted in the recited definition of the epitope to which antibodies of the invention bind. A-834735 differs from XLR-11 and UR-144 in having a methyl pyran N-side chain. It is hypothesised that the additional molecular length and rotational flexibility that the carboxamide group imparts, as well as, the powerful epitopic potential of the —NH— atom through hydrogen bonding and the absence of the adamantyl group would explain why UR-144 and XLR-11 do not bind to the antibodies of the invention.

JWH-203 shares a 1-pentylindazol-3-ylmethanone with AKB48 and incorporates a carboxamide group between the indole ring system and the rest of the molecule, in this case, a 2-chlorophenyl ring. The absence of the adamantyl group would explain why JWH-203 does not bind to the antibodies of the invention.

AM-694 shares a 1-pentylindol-3-yl methanone with AKB48, but incorporates a ketone group between the indole ring system and the other ring, in this case, a 2-iodophenyl ring. AM-694 has a 5-fluoro substitution on the pentyl side chain, permitted in the recited definition of the epitope to which antibodies of the invention bind. It is hypothesised that the additional molecular length and rotational flexibility that the carboxamide group imparts, as well as, the powerful epitopic potential of the —NH— atom through hydrogen bonding and the absence of the adamantyl group would explain why AM-694 does not bind to the antibodies of the invention.

JWH-200 shares an indol-3-yl methanone with AKB48, but incorporates a ketone group between the indole ring system and the other ring, in this case, a naphthalene ring. JWH-200 differs from AKB48 in having 2-morpholin-ethyl N-side chain, not permitted in the recited definition of the epitope to which antibodies of the invention bind. JWH-073 differs from JWH-200 in having an N-butyl side chain. JWH-073 4-Hydroxyindole and JWH-073 5-Hydroxyindole each differ from JWH-073 in having an OH substitution on the indole ring. It is hypothesised that the additional molecular length and rotational flexibility that the carboxamide group imparts, as well as, the powerful epitopic potential of the —NH— atom through hydrogen bonding and the absence of the adamantyl group would explain why JWH-200 and JWH-073 and its derivatives do not bind to the antibodies of the invention.

JWH-250 N-(5-Carboxypentyl) and JWH-250 N-(5-Hydroxypentyl) are derivatives of JWH-250. JWH-250 shares a 1-pentylindazol-3-yl methanone with AKB48 and incorporates a carboxamide group between the indole ring system and the rest of the molecule, in this case, a 2-methoxyphenyl ring. JWH-250 N-(5-Carboxypentyl) and JWH-250 N-(5-Hydroxypentyl) differ from JWH-250 in the identity of the N-side chain. At least the absence of the adamantyl group would explain why these derivatives of JWH-250 do not bind to the antibodies of the invention.

Taken together, the cross reactivity data of Table 2 suggest that the antibodies of the present invention require:

A substituted or unsubstituted adamantane ring. Under the conditions of Example 12, there was a cross reactivity of less than 2%, optionally, less than 1%, when the adamantane ring is replaced with substituted or unsubstituted naphthalene, substituted or unsubstituted phenyl, quinolone, quinolone or a tetramethyl cyclopropane or when the adamantane ring is absent (AB Pinaca);

A heterocyclic ring selected from an indole or an indazole. Optionally, the indole and the indazole are unsubstituted. If the heterocyclic ring is substituted, this might comprise a 4-OH, a 5-OH, a 6-OH or a 2-methoxy;

A carboxamide group linking the heterocyclic ring with the adamantane ring. Under the conditions of Example 12, there was a cross reactivity of less than 2%, optionally, less than 1%, when the carboxamide group was replaced with a ketone (see derivatives of AB001);

An N-substituted or unsubstituted alkyl or alkenyl of $C_4$ to $C_6$; optionally, $C_4$ or $C_5$, further optionally, $C_5$. The alkyl can, preferably, terminate in a halo, optionally, F, substituent. A terminal nitrile is also envisaged, as is an OH (either terminal or on the C adjacent the terminal C). The alkyl should not terminate with a COOH substituent (see AKB48 and SDB-001 when compared to the corresponding substances terminating with a COOH). The alkyl or alkenyl should not be substituted with a piperidine.

The current invention enables sensitive detection of AKB48 and analogues and detection of 3-OH-AKB48 at a high level of sensitivity.

The invention claimed is:
1. A polyclonal antibody derived from an immunogen having the structure:

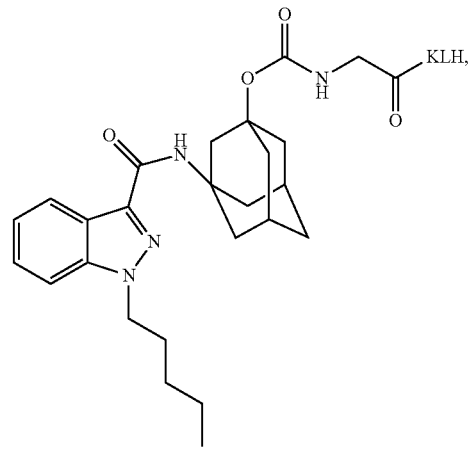

wherein KLH is keyhole limpet hemocyanin;
wherein the polyclonal antibody binds to one or more epitopes of one or more molecules of Structure I',

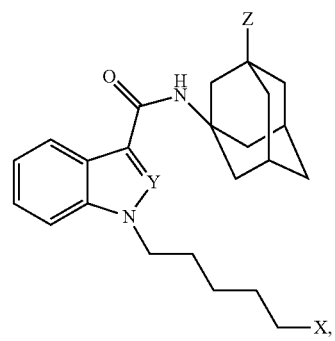

Structure I' wherein X is H or F; Y is N or CH; and Z is H or OH; and wherein the polyclonal antibody has an $IC_{50}$ of 0.18 ng/ml for 3-OH-AKB48, 2.08 ng/ml for AKB-48, 2.10 ng/ml for N-(5-fluoropentyl)-AKB48 and 4.40 ng/ml for 3-OH-SDB001, and <1.00% cross-reactivity with AKB48 N-Pentanoic acid compared to 100% cross-reactivity with AKB48, wherein the $IC_{50}$ values and cross-reactivity are determined by employing a tracer having the structure:

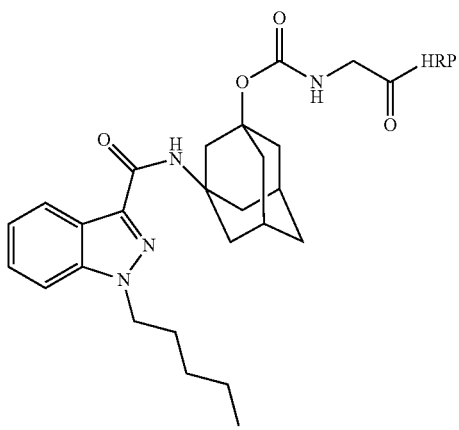

wherein HRP is horseradish peroxidase.

2. A solid state device supporting the polyclonal antibody of claim 1.

3. The solid state device of claim 2 which is a biochip or a microtitre plate.

4. A kit for the detection or determination of compounds of Structure I',

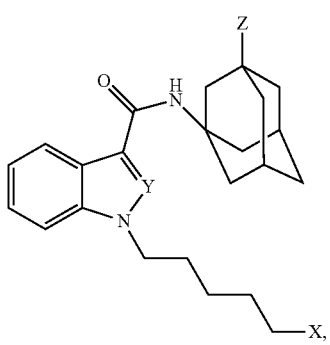

wherein X is H or F; Y is N or CH; and Z is H or OH, comprising the polyclonal antibody of claim 1.

5. An immunoassay method for detecting or determining compounds of Structure I'

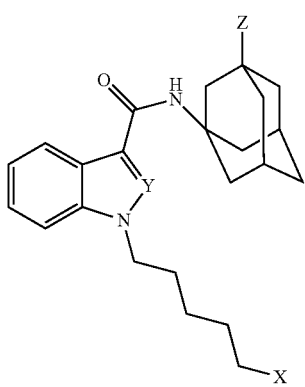

wherein X is H or F; Y is N or CH; and Z is H or OH;

the method comprising contacting a solution or an in vitro sample taken from an individual suspected of containing compounds of Structure I' with the polyclonal antibody of claim 1; and one or more detecting agents;

measuring the signal produced by the one or more detecting agent; and deducing from a calibrator the presence of, or amount of, compounds of Structure I'.

6. The immunoassay method of claim 1 wherein the detecting agent comprises:

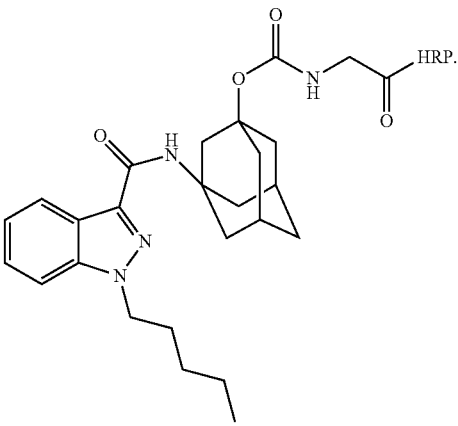

7. A method of making an antibody comprising:
administering an immunogen having the structure of:

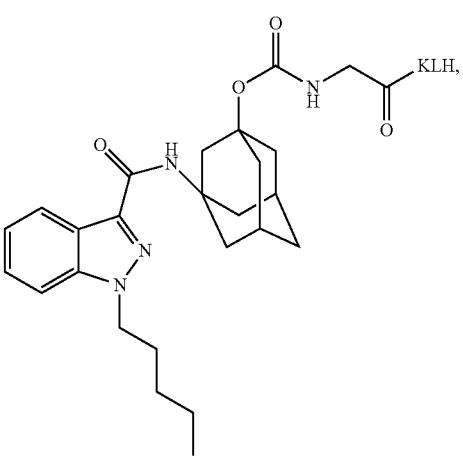

wherein KLH is keyhole limpet hemocyanin,
to a mammal; and
purifying the resultant antibody.

8. The method of claim 7, wherein the antibody is a polyclonal antibody.

* * * * *